(12) United States Patent
Eshoo et al.

(10) Patent No.: US 9,803,188 B2
(45) Date of Patent: Oct. 31, 2017

(54) SYSTEMS AND METHODS FOR ISOLATING NUCLEIC ACIDS

(71) Applicant: IBIS BIOSCIENCES, INC., Carlsbad, CA (US)

(72) Inventors: Mark W. Eshoo, San Diego, CA (US); Christopher Crowder, San Marcos, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 443 days.

(21) Appl. No.: 14/367,796

(22) PCT Filed: Dec. 21, 2012

(86) PCT No.: PCT/US2012/071372
§ 371 (c)(1),
(2) Date: Jun. 20, 2014

(87) PCT Pub. No.: WO2013/096838
PCT Pub. Date: Jun. 27, 2013

(65) Prior Publication Data
US 2014/0323319 A1    Oct. 30, 2014

Related U.S. Application Data

(60) Provisional application No. 61/579,507, filed on Dec. 22, 2011.

(51) Int. Cl.
C12N 15/10    (2006.01)
C12Q 1/70    (2006.01)
C12Q 1/68    (2006.01)

(52) U.S. Cl.
CPC ....... *C12N 15/1013* (2013.01); *C12Q 1/6806* (2013.01); *C12Q 1/701* (2013.01)

(58) Field of Classification Search
None
See application file for complete search history.

(56) References Cited

U.S. PATENT DOCUMENTS

| | | | |
|---|---|---|---|
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,130,238 A | 7/1992 | Malek et al. |
| 5,270,184 A | 12/1993 | Walker et al. |
| 5,283,174 A | 2/1994 | Arnold, Jr. et al. |
| 5,399,491 A | 3/1995 | Kacian et al. |
| 5,455,166 A | 10/1995 | Walker |
| 5,480,784 A | 1/1996 | Kacian et al. |
| 5,695,934 A | 12/1997 | Brenner |
| 5,710,029 A | 1/1998 | Ryder et al. |
| 5,714,330 A | 2/1998 | Brenner et al. |
| 5,750,341 A | 5/1998 | MacEvicz |
| 5,807,527 A | 9/1998 | Burgoyne |
| 5,814,447 A | 9/1998 | Ishiguro et al. |
| 5,824,518 A | 10/1998 | Kacian et al. |
| 5,912,148 A | 6/1999 | Eggerding |
| 5,925,517 A | 7/1999 | Tyagi et al. |
| 5,928,862 A | 7/1999 | Morrison |
| 6,130,073 A | 10/2000 | Eggerding |
| 6,150,097 A | 11/2000 | Tyagi et al. |
| 6,168,922 B1 | 1/2001 | Harvey et al. |
| 6,210,891 B1 | 4/2001 | Nyren et al. |
| 6,258,568 B1 | 7/2001 | Nyren |
| 6,303,305 B1 | 10/2001 | Wittwer et al. |
| 6,306,597 B1 | 10/2001 | MacEvicz |
| 6,432,360 B1 | 8/2002 | Church |
| RE37,891 E | 10/2002 | Collins et al. |
| 6,485,944 B1 | 11/2002 | Church et al. |
| 6,511,803 B1 | 1/2003 | Church et al. |
| 6,534,274 B2 | 3/2003 | Becker et al. |
| 6,541,205 B1 | 4/2003 | Yokoyama et al. |
| 6,787,308 B2 | 9/2004 | Balasubramanian et al. |
| 6,818,395 B1 | 11/2004 | Quake et al. |
| 6,833,246 B2 | 12/2004 | Balasubramanian |
| 6,911,345 B2 | 6/2005 | Quake et al. |
| 6,969,488 B2 | 11/2005 | Bridgham et al. |
| 7,108,974 B2 | 9/2006 | Ecker et al. |
| 7,115,400 B1 | 10/2006 | Adessi et al. |
| 7,169,560 B2 | 1/2007 | Lapidus et al. |
| 7,282,337 B1 | 10/2007 | Harris |
| 7,482,120 B2 | 1/2009 | Buzby |
| 7,501,245 B2 | 3/2009 | Quake et al. |

(Continued)

FOREIGN PATENT DOCUMENTS

| | | |
|---|---|---|
| EP | 0684315 A1 | 11/1995 |
| WO | WO-0018957 A1 | 4/2000 |
| WO | WO-2006084132 A2 | 8/2006 |

OTHER PUBLICATIONS

Adessi C., et al., "Solid Phase DNA Amplification: Characterisation of Primer Attachment and Amplification Mechanisms," Nucleic Acids Research, 2000, vol. 28 (20), pp. E87.

Astier Y., et al., "Toward Single Molecule DNA Sequencing: Direct Identification of Ribonucleoside and Deoxyribonucleoside 5'-monophosphates by Using an Engineered Protein Nanopore Equipped with a Molecular Adapter," Journal of the American Chemical Society, 2006, vol. 128 (5), pp. 1705-1710.

Bennett S.T., et al., "Toward the 1,000 Dollars Human Genome," Pharmacogenomics, 2005, vol. 6 (4), pp. 373-382.

Birren B., et al., eds., Genome Analysis—A Laboratory Manual, vol. 1, Cold Spring Harbor Laboratory Press, 1997, Table of Contents.

Branton D., et al., "The Potential and Challenges of Nanopore Sequencing," Nature Biotechnology, 2008, vol. 26 (10), pp. 1146-1153.

Brenner S., et al., "Gene Expression Analysis by Massively Parallel Signature Sequencing (MPSS) on Microbead Arrays," Nature Biotechnology, 2000, vol. 18 (6), pp. 630-634.

(Continued)

*Primary Examiner* — David Thomas
(74) *Attorney, Agent, or Firm* — David A. Casimir; Casimir Jones, S.C.

(57) ABSTRACT

The present disclosure relates to systems and methods for nucleic acid isolation. In particular, the present disclosure provides systems and methods for isolating nucleic acids from aqueous samples (e.g., blood or urine).

14 Claims, 5 Drawing Sheets

(56) References Cited

U.S. PATENT DOCUMENTS

| | | | |
|---|---|---|---|
| 8,017,322 | B2 | 9/2011 | Ecker et al. |
| 8,017,743 | B2 | 9/2011 | Ecker et al. |
| 2004/0224344 | A1 | 11/2004 | Han et al. |
| 2005/0042638 | A1 | 2/2005 | Arnold et al. |
| 2005/0130173 | A1 | 6/2005 | Leamon et al. |
| 2006/0046265 | A1 | 3/2006 | Becker et al. |
| 2009/0026082 | A1 | 1/2009 | Rothberg et al. |
| 2009/0035777 | A1 | 2/2009 | Kokoris et al. |
| 2009/0127589 | A1 | 5/2009 | Rothberg et al. |
| 2010/0137143 | A1 | 6/2010 | Rothberg et al. |
| 2010/0188073 | A1 | 7/2010 | Rothberg et al. |
| 2010/0197507 | A1 | 8/2010 | Rothberg et al. |
| 2010/0301398 | A1 | 12/2010 | Rothberg et al. |
| 2010/0317014 | A1 | 12/2010 | Eshoo et al. |
| 2011/0172409 | A1 | 7/2011 | Han |
| 2014/0212868 | A1* | 7/2014 | Wilmes .................. C12N 1/066 435/6.1 |

OTHER PUBLICATIONS

Co-pending U.S. Appl. No. 11/671,956, filed Feb. 6, 2007.
Co-pending U.S. Appl. No. 11/781,166, filed Jul. 20, 2007.
Drmanac S., et al., "Accurate Sequencing by Hybridization for DNA Diagnostics and Individual Genomics," Nature Biotechnology, 1998, vol. 16 (1), pp. 54-58.
Eid J., et al., "Real-time Dna Sequencing from Single Polymerase Molecules," Science, 2009, vol. 323 (5910), pp. 133-138.
Guatelli J.C., et al., "Isothermal, in Vitro Amplification of Nucleic Acids by a Multienzyme Reaction Modeled after Retroviral Replication," Proceedings of the National Academy of Sciences, 1990, vol. 87 (5), pp. 1874-1878.
Harris T.D., et al., "Single-molecule Dna Sequencing of a Viral Genome," Science, 2008, vol. 320 (5872), pp. 106-109.
International Search Report and Written Opinion for Application No. PCT/US2012/071372, mailed on Mar. 5, 2013, 9 pages.
Kato K., "Impact of the Next Generation Dna Sequencers," International Journal of Clinical and Experimental Medicine, 2009, vol. 2 (2), pp. 193-202.
Korlach J., et al., "Selective Aluminum Passivation for Targeted Immobilization of Single DNA Polymerase Molecules in Zero-Mode Waveguide Nanostructures," Proceedings of the National Academy of Sciences, 2008, vol. 105 (4), pp. 1176-1181.
Kwoh D.Y., et al., "Transcription-Based Amplification System and Detection of Amplified Human Immunodeficiency Viru: Type 1 with a Bead-Based Sandwixh Hybridization Format," Proceeding of the National Academy of Sciences of the USA, 1989, vol. 86 (4), pp. 1173-1177.
Levene M.J., et al., "Zero-mode Waveguides for Single-molecule Analysis at High Concentrations," Science, 2003, vol. 299 (5607), pp. 682-686.

Lizardi P.M., et al., "Exponential Amplification of Recombinant—RNA Hybridization Probes," Bio/Technology, 1988, vol. 6, pp. 1197-1202.
MacLean D., et al., "Application of 'next-generation' Sequencing Technologies to Microbial Genetics," Nature Reviews Microbiology, 2009, vol. 7 (4), pp. 287-296.
Margulies M., et al., "Genome Sequencing in Microfabricated High-Density Picolitre Reactors," Nature, 2005, vol. 437 (7057), pp. 376-380.
Maxam A.M., et al., "A New Method for Sequencing Dna," Proceedings of the National Academy of Sciences of the United States of America, 1977, vol. 74 (2), pp. 560-564.
Michaud C.L., et al., "Simplified Field Preservation of Tissues for Subsequent DNA Analyses," Journal of Forensic Sciences, 2011, vol. 56 (4), pp. 846-852.
Mitra R.D., et al., "Fluorescent in Situ Sequencing on Polymerase Colonies," Analytical Biochemistry, 2003, vol. 320 (1), pp. 55-65.
Morozova O., et al., "Applications of Next-generation Sequencing Technologies in Functional Genomics," Genomics, 2008, vol. 92 (5), pp. 255-264.
Mullis K.B., et al., "Specific Synthesis of Dna In Vitro Via a Polymerase-catalyzed Chain Reaction," Methods in Enzymology, 1987, vol. 155, pp. 335-350.
Murakawa G. J., et al., "Direct detection of HIV-1 RNA from AIDS and ARC patient samples", DNA., 1988, 7 (4), 287-295.
Pennisi E., "Genomics. Semiconductors Inspire New Sequencing Technologies," Science, 2010, vol. 327 (5970), pp. 1190.
Persing, "In Vitro Nucleic Acid Amplification Techniques," Diagnostic Molecular Microbiology, 1993, pp. 51-77.
Ronaghi M., et al., "Real-time Dna Sequencing Using Detection of Pyrophosphate Release," Analytical Biochemistry, 1996, vol. 242 (1), pp. 84-89.
Ruparel H., et al., "Design and Synthesis of a 3'-o-allyl Photocleavable Fluorescent Nucleotide as a Reversible Terminator for Dna Sequencing by Synthesis," Proceedings of the National Academy of Sciences of the United States of America, 2005, vol. 102 (17), pp. 5932-5937.
Sanger F., et al., "DNA Sequencing with Chain-Terminating Inhibitors," Proceedings of the National Academy of Sciences, 1977, vol. 74 (12), pp. 5463-5467.
Shendure J., et al., "Accurate Multiplex Polony Sequencing of an Evolved Bacterial Genome," Science, 2005, vol. 309 (5741), pp. 1728-1732.
Voelkerding K.V., et al., "Next-Generation Sequencing: from Basic Research to Diagnostics," Clinical Chemistry, 2009, vol. 55 (4), pp. 641-658.
Walker G.T., et al., "Isothermal in Vitro Amplification of DNA by a Restriction Enzyme/DNA Polymerase System," Proceedings of the National Academy of Sciences, 1992, vol. 89 (1) pp. 392-396.
Weiss R., "Hot Prospect for New Gene Amplifier," Science, 1991, vol. 254 (5036), pp. 1292-1293.

* cited by examiner

SYSTEMS AND METHODS FOR ISOLATING NUCLEIC ACIDS

FIELD OF INVENTION

The present disclosure relates to systems and methods for nucleic acid isolation. In particular, the present disclosure provides systems and methods for isolating nucleic acids from aqueous samples (e.g., blood or urine).

BACKGROUND

Nucleic acids found in cells can be deoxyribonucleic acid or ribonucleic acid and can be genomic DNA, extrachromosomal DNA (e.g. plasmids and episomes), mitochondrial DNA, messenger RNA and transfer RNA. Nucleic acids can also be foreign to the host and contaminate a cell as an infectious agent, e.g. bacteria, viruses, fungi or single celled organisms and infecting multicellular organisms (parasites). Recently, detection and analysis of the presence of nucleic acids has become important for the identification of single nucleotide polymorphisms (SNPs), chromosomal rearrangements and the insertion of foreign genes. These include infectious viruses, e.g. HIV and other retroviruses, jumping genes, e.g. transposons, and the identification of nucleic acids from recombinantly engineered organisms containing foreign genes, e.g. Roundup Ready™ plants.

The analysis of nucleic acids has a wide array of uses. For example, the presence of a foreign agent can be used as a medical diagnostic tool. The identification of the genetic makeup of cancerous tissues can also be used as a medical diagnostic tool, confirming that a tissue is cancerous, and determining the aggressive nature of the cancerous tissue. Chromosomal rearrangements, SNPs and abnormal variations in gene expression can be used as a medical diagnostic for particular disease states. Further, genetic information can be used to ascertain the effectiveness of particular pharmaceutical drugs, known as the field of pharmacogenomics. Genetic variations between humans and between domestic animals can also be ascertained by DNA analysis. This is used in fields including forensics, paternity testing and animal husbandry.

Methods of extracting nucleic acids from cells are well known to those skilled in the art. A cell wall can be weakened by a variety of methods, permitting the nucleic acids to extrude from the cell and permitting its further purification and analysis. The specific method of nucleic acid extraction is dependent on the type of nucleic acid to be isolated, the type of cell, and the specific application used to analyze the nucleic acid. Many methods of isolating DNA are known to those skilled in the art, see for example the general reference Sambrook and Russell, 2001, "Molecular Cloning: A Laboratory Manual". For example, the prior art contains examples of chemically-impregnated and dehydrated solid-substrates for the extraction and isolation of DNA from bodily fluids that employ lytic salts and detergents and which contain additional reagents for long-term storage of DNA samples e.g. U.S. Pat. No. 5,807,527 detailing FTA paper and U.S. Pat. No. 6,168,922 detailing Isocard Paper. The prior art also contains examples of particle separation methods, e.g. U.S. RE 37,891.

Methods of isolating RNA, particularly messenger RNA (mRNA) are well known to those skilled in the art. Typically, cell disruption is performed in the presence of strong protein denaturing solutions, which inactivate RNAses during the RNA isolation procedure. RNA is then isolated using differential ethanol precipitation with centrifugation. As is well known, RNA is extremely labile and is sensitive to alkaline conditions, as well as RNAses, which degrade RNA. RNAses are ubiquitous within the environment and it has been found that they are difficult to remove from solutions and containers used to isolate RNA.

While many nucleic acid purification procedures are well known and have been in existence for years, these procedures can be time consuming and may employ reagents that present dangers to those performing the purification. For example, it has long been known that DNA and RNA readily can be obtained in a purified form from a test sample using organic extraction procedures, but such procedures can require several extractions and therefore can be time consuming. Additionally, the use of organic solvents is undesirable and dangerous if proper precautions are not followed.

Accordingly, there is a need for a safe, effective and convenient method for isolating nucleic acids from cells. Methods for simultaneously isolating RNA from DNA are particularly needed.

SUMMARY

The present disclosure relates to systems and methods for nucleic acid isolation. In particular, the present disclosure provides systems and methods for isolating nucleic acids from aqueous samples (e.g., blood or urine).

The present disclosure provides improved methods of simultaneously isolating both DNA and RNA from a single biological sample. The ability to only perform one process results in cost savings and decreased discomfort for subjects.

For example, in some embodiments, the present invention provides a method of simultaneously extracting DNA and RNA from a sample, comprising: a) contacting a sample with an alcohol (e.g., isopropanol); b) lysing the sample by incubating in a lysis solution to generate a lysed sample (e.g., at approximately 30° C. for approximately 1 hour); and c) extracting nucleic acids from the lysed sample to generate extracted nucleic acids. In some embodiments, the sample is an aqueous biological fluid (e.g., including but not limited to, blood, blood products, or urine). In some embodiments, the contacting step a) occurs prior to the lysis step b). In some embodiments, the method further comprises the step of disrupting cell walls in said sample prior to the contacting step a) (e.g., by bead beating in the presence of a detergent). In some embodiments, extracting step c) comprises binding the nucleic acids to a bead or solid support.

In some embodiments, the method further comprises the step of analyzing the extracted nucleic acids for the presence of a target DNA and/or RNA. In some embodiments, the target nucleic acid is a pathogen (e.g., a virus, fungus or bacteria). In some embodiments, the analysis comprises, for example, a method selected from an amplification method, a sequencing method, or a hybridization method.

In some embodiments, the method is automated (e.g., by using robotic sample handling and analysis systems).

Further embodiments of the present invention provide kits and systems comprising components necessary, sufficient or useful for performing the described methods (e.g., reagents, controls, instructions, etc.).

Additional embodiments will be apparent to persons skilled in the relevant art based on the teachings contained herein.

BRIEF DESCRIPTION OF THE DRAWINGS

These and other features, aspects, and advantages of the present technology will become better understood with regard to the following drawings.

DETAILED DESCRIPTION

Figure 1:
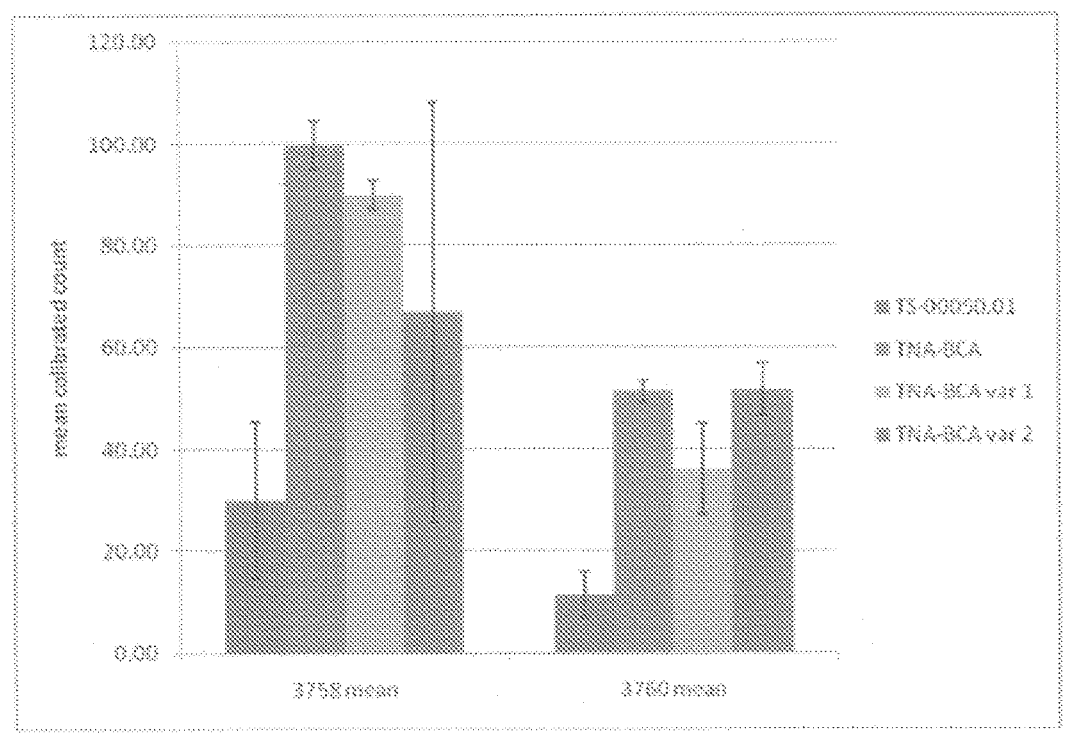
FIG. 1 shows detection of Coxsackie RNA virus on primer pairs VIR3758 and VIR3760 using methods of embodiments of the present invention.

The present disclosure relates to systems and methods for nucleic acid isolation. In particular, the present disclosure provides systems and methods for isolating nucleic acids from aqueous samples (e.g., blood or urine).

Definitions

To facilitate an understanding of the present technology, a number of terms and phrases are defined below. Additional definitions are set forth throughout the detailed description. As used herein, "a" or "an" or "the" can mean one or more than one. For example, "a" widget can mean one widget or a plurality of widgets.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. If double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "target," when used in reference to the polymerase chain reaction, refers to the region of nucleic acid bounded by the primers used for polymerase chain reaction. Thus, the "target" is sought to be sorted out from other nucleic acid sequences. A "segment" is defined as a region of nucleic acid within the target sequence.

As used herein, the terms "subject" and "patient" refer to any animal, such as a dog, a cat, a bird, livestock, and particularly a mammal, and preferably a human.

As used herein, the term "sample" is used in its broadest sense. In one sense, it is meant to include a representative portion or culture obtained from any source, including biological and environmental sources. Biological samples may be obtained from animals (including humans) and encompass fluids, solids, tissues, and gases. Biological samples include blood products, such as plasma, serum, and the like. Environmental samples include environmental material such as surface matter, soil, mud, sludge, biofilms, water, and industrial samples. Such examples are not however to be construed as limiting the sample types applicable to the present invention.

EMBODIMENTS OF THE TECHNOLOGY

Although the disclosure herein refers to certain illustrated embodiments, it is to be understood that these embodiments are presented by way of example and not by way of limitation.

Embodiments of the present invention provide kits, systems and methods for isolating DNA and RNA from biological samples (e.g., aqueous samples such as blood, urine, blood products and the like). The kits, systems, and methods described herein find use in research, screening, diagnostic, clinical, and therapeutic applications.

In addition to bacteria and DNA viruses pathogens can be RNA viruses. Embodiments of the present invention provide the ability to extract both DNA and RNA simultaneously in a single process, which allows detection of both DNA and RNA based organisms without any prior knowledge of what might be present.

The ability to isolate nucleic acids from urine is also advantageous since it is a much easier and less invasive procedure to a patient. By being able to isolate nucleic acids from urine, including that from pathogens, it is possible to detect active infections in an individual without having to draw a blood sample.

The present disclosure provides the advantage of the ability to isolate both DNA and RNA from a single sample. This requires less time, sample, and handling then having to perform two separate extractions; one for DNA and one for RNA. Experiments conducted during the course of development of embodiments of the present invention demonstrated that the methods described herein resulted in more DNA retrieved from urine then from a commercially available urine DNA isolation kit.

Accordingly, in some embodiments, the present invention provides kits, systems and methods for simultaneously isolating DNA and RNA from biological samples. The present invention is not limited to a particular sample. Examples of biological samples (e.g., aqueous samples) suitable for use with the described methods include, but are not limited to, whole blood, blood products (e.g., serum), urine, semen, lymph fluid, saliva, tears, mucus, etc.

The present invention is not limited to a particular source of nucleic acids for isolation. In some embodiments, nucleic acids are mammalian. In other embodiments, nucleic acids from foreign pathogens (e.g., viruses, bacteria, fungi, etc.) are isolated. In some particular embodiments, the presence of blood or urine borne pathogens is detected.

In some embodiments, the methods of nucleic acid isolation comprise the following steps: a) breaking cell walls (e.g., using any suitable method including but not limited to bead beating in the presence of detergent); b) treating the lysate with an alcohol (e.g., ethanol or isopropanol); c) incubating in the presence of the alcohol (e.g., at approximately 30° C.) for a period of approximately 1 hour, although other incubation temperatures and times may be utilized; and d) extracting nucleic acids from the lysed sample (e.g., using any suitable method, including, but not limited to, binding to beads or particles).

In some embodiments, one or more steps are automated (e.g., using automated sample handling or robotics).

Following isolation, nucleic acids may be analyzed using any suitable method. In some embodiments, the presence of pathogens is detected (e.g., blood or urine borne pathogens). In other embodiments, the presence of nucleic acid variants, polymorphisms, mutations, etc. are detected.

Examples of nucleic acid detection methods include, but are not limited to, sequencing, amplification, microarrays, probe binding and the like. Exemplary methods are described below.

A. Sequencing

Illustrative non-limiting examples of nucleic acid sequencing techniques include, but are not limited to, chain terminator (Sanger) sequencing and dye terminator sequencing. Those of ordinary skill in the art will recognize that because RNA is less stable in the cell and more prone to nuclease attack experimentally RNA is usually reverse transcribed to DNA before sequencing.

Chain terminator sequencing uses sequence-specific termination of a DNA synthesis reaction using modified nucleotide substrates. Extension is initiated at a specific site on the template DNA by using a short radioactive, or other labeled, oligonucleotide primer complementary to the template at that region. The oligonucleotide primer is extended using a DNA polymerase, standard four deoxynucleotide bases, and a low concentration of one chain terminating nucleotide, most commonly a di-deoxynucleotide. This reaction is repeated in four separate tubes with each of the bases taking turns as the di-deoxynucleotide. Limited incorporation of the chain terminating nucleotide by the DNA polymerase results in a series of related DNA fragments that are terminated only at positions where that particular di-deoxynucleotide is used. For each reaction tube, the fragments are size-separated by electrophoresis in a slab polyacrylamide gel or a capillary tube filled with a viscous polymer. The sequence is determined by reading which lane produces a visualized mark from the labeled primer as you scan from the top of the gel to the bottom.

Dye terminator sequencing alternatively labels the terminators. Complete sequencing can be performed in a single reaction by labeling each of the di-deoxynucleotide chain-terminators with a separate fluorescent dye, which fluoresces at a different wavelength.

A variety of nucleic acid sequencing methods are contemplated for use in the methods of the present disclosure including, for example, chain terminator (Sanger) sequencing, dye terminator sequencing, and high-throughput sequencing methods. Many of these sequencing methods are well known in the art. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

In some embodiments, the technology provided herein finds use in a Second Generation (a.k.a. Next Generation or Next-Gen), Third Generation (a.k.a. Next-Next-Gen), or Fourth Generation (a.k.a. N3-Gen) sequencing technology including, but not limited to, pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies in *Genomics,* 92: 255 (2008), herein incorporated by reference in its entirety. Those of ordinary skill in the art will recognize that because RNA is less stable in the cell and more prone to nuclease attack experimentally RNA is usually reverse transcribed to DNA before sequencing.

A number of DNA sequencing techniques are known in the art, including fluorescence-based sequencing methodologies (See, e.g., Birren et al., Genome Analysis: Analyzing DNA, 1, Cold Spring Harbor, N.Y.; herein incorporated by reference in its entirety). In some embodiments, the technology finds use in automated sequencing techniques understood in that art. In some embodiments, the present technology finds use in parallel sequencing of partitioned amplicons (PCT Publication No: WO2006084132 to Kevin McKernan et al., herein incorporated by reference in its entirety). In some embodiments, the technology finds use in DNA sequencing by parallel oligonucleotide extension (See, e.g., U.S. Pat. No. 5,750,341 to Macevicz et al., and U.S. Pat. No. 6,306,597 to Macevicz et al., both of which are herein incorporated by reference in their entireties). Additional examples of sequencing techniques in which the technology finds use include the Church polony technology (Mitra et al., 2003, Analytical Biochemistry 320, 55-65; Shendure et al., 2005 Science 309, 1728-1732; U.S. Pat. No. 6,432,360, U.S. Pat. No. 6,485,944, U.S. Pat. No. 6,511,803; herein incorporated by reference in their entireties), the 454 picotiter pyrosequencing technology (Margulies et al., 2005 Nature 437, 376-380; US 20050130173; herein incorporated by reference in their entireties), the Solexa single base addition technology (Bennett et al., 2005, Pharmacogenomics, 6, 373-382; U.S. Pat. No. 6,787,308; U.S. Pat. No. 6,833,246; herein incorporated by reference in their entireties), the Lynx massively parallel signature sequencing technology (Brenner et al. (2000). Nat. Biotechnol. 18:630-634; U.S. Pat. No. 5,695,934; U.S. Pat. No. 5,714,330; herein incorporated by reference in their entireties), and the Adessi PCR colony technology (Adessi et al. (2000). Nucleic Acid Res. 28, E87; WO 00018957; herein incorporated by reference in its entirety).

Next-generation sequencing (NGS) methods share the common feature of massively parallel, high-throughput strategies, with the goal of lower costs in comparison to older sequencing methods (see, e.g., Voelkerding et al., *Clinical Chem.,* 55: 641-658, 2009; MacLean et al., *Nature Rev. Microbiol.,* 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

In pyrosequencing (Voelkerding et al., *Clinical Chem.,* 55: 641-658, 2009; MacLean et al., *Nature Rev. Microbiol.,* 7: 287-296; U.S. Pat. No. 6,210,891; U.S. Pat. No. 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., Clinical Chem., 55: 641-658, 2009; MacLean et al., Nature Rev. Aicrobiol., 7: 287-296; U.S. Pat. No. 6,833,246; U.S. Pat. No. 7,115,400; U.S. Pat. No. 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 50 nucleotides, with overall output exceeding 1 billion nucleotide pairs per analytical run.

Sequencing nucleic acid molecules using SOLiD technology (Voelkerding et al., Clinical Chem., 55: 641-658, 2009; MacLean et al., Nature Rev. Microbiol., 7: 287-296; U.S. Pat. No. 5,912,148; U.S. Pat. No. 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, the technology finds use in nanopore sequencing (see, e.g., Astier et al., J. Am. Chem. Soc. 2006 Feb. 8; 128(5): 1705-10, herein incorporated by reference). The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, the technology finds use in HeliScope by Helicos BioSciences (Voelkerding et al., Clinical Chem., 55: 641-658, 2009; MacLean et al., Nature Rev. Microbiol., 7: 287-296; U.S. Pat. No. 7,169,560; U.S. Pat. No. 7,282,337; U.S. Pat. No. 7,482,120; U.S. Pat. No. 7,501,245; U.S. Pat. No. 6,818,395; U.S. Pat. No. 6,911,345; U.S. Pat. No. 7,501,245; each herein incorporated by reference in their entirety). Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., Science 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb generated per run. The read-length is 100 base pairs. The accuracy for homopolymer repeats of 5 repeats in length is ~98%. The benefits of ion semiconductor sequencing are rapid sequencing speed and low upfront and operating costs.

The technology finds use in another nucleic acid sequencing approach developed by Stratos Genomics, Inc. and involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., *Clinical Chem.*, 55: 641-58, 2009; U.S. Pat. No. 7,329,492; U.S. patent application Ser. No. 11/671,956; U.S. patent application Ser. No. 11/781, 166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

B. Hybridization

Illustrative non-limiting examples of nucleic acid hybridization techniques include, but are not limited to, microarrays including, but not limited to: DNA microarrays (e.g., eDNA microarrays and oligonucleotide microarrays). A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microclectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

C. Amplification

Nucleic acids may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and U.S. Pat. No. 4,800,159; Mullis et al., *Meth. Enzymol.* 155: 335 (1987); and, Murakawa et al., *DNA* 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265 (herein incorporated by reference in its entirety), TMA optionally incorporates the use of blocking moieties, terminating moieties, and other modifying moieties to improve TMA process sensitivity and accuracy.

The ligase chain reaction (Weiss, R., *Science* 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., *Proc. Natl. Acad. Sci. USA* 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPαS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0 684 315).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., *BioTechnol.* 6: 1197 (1988), herein incorporated by reference in its entirety), commonly referred to as Qβ replicase; a transcription based amplification method (Kwoh et al., Proc. Natl. Acad. Sci. USA 86:1173 (1989)); and, self-sustained sequence replication (Guatelli et al., *Proc. Natl. Acad. Sci. USA* 87: 1874 (1990), each of which is herein incorporated by reference in its entirety). For further discussion of known amplification methods see Persing, David H., "In Vitro Nucleic Acid Amplification Techniques" in *Diagnostic Medical Microbiology: Principles and Applications* (Persing et al., Eds.), pp. 51-87 (American Society for Microbiology, Washington, D.C. (1993)).

D. Detection Methods

Non-amplified or amplified nucleic acids can be detected by any conventional means. For example, the nucleic acids can be detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541,205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DABCYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention. Probe systems used to detect single nucleotide polymorphisms (SNPs) might also be utilized in the present invention. Additional detection systems include "molecular switches," as disclosed in U.S. Publ. No. 20050042638, herein incorporated by reference in its entirety. Other probes, such as those comprising intercalating dyes and/or fluorochromes, are also useful for detection of amplification products in the present invention. See, e.g., U.S. Pat. No. 5,814,447 (herein incorporated by reference in its entirety).

In some embodiments, nucleic acids are detected and characterized by the identification of a unique base composition signature (BCS) using mass spectrometry (e.g., Abbott PLEX-ID system, Abbot Ibis Biosciences, Abbott Park, Ill.,) described in U.S. Pat. Nos. 7,108,974, 8,017,743, and 8,017,322; each of which is herein incorporated by reference in its entirety.

In some embodiments, a computer-based analysis program is used to translate the raw data generated by the detection assay (e.g., the presence, absence, or amount of a given nucleic acid) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum or urine sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., expression data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., presence or absence of a nucleic acid) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

E. Systems and Kits

In some embodiments, the present invention provides kits and systems for the lysis, isolation, and analysis of nucleic acids (e.g., DNA and/or RNA). In some embodiments, kits include reagents necessary, sufficient or useful for detection of nucleic acids (e.g., reagents, controls, instructions, etc.). In some embodiments, systems include automated sample and reagent handling devices (e.g., robotics).

EXPERIMENTAL

The following examples are provided in order to demonstrate and further illustrate certain preferred embodiments and aspects of the present invention and are not to be construed as limiting the scope thereof.

Example 1

Whole blood samples were obtained from a commercial source. To show nucleic acid yield was from recovery of RNA as well as DNA, stocks of a Coxsackie virus (an RNA virus) were made to spike into blood samples to use as a comparator between methods.

To show RNA recovery with the protocol, the results were compared to an existing protocol for isolation of both DNA and RNA from blood using Qiagen columns.

Spiked blood samples were made by adding 10 µL of the previously made Coxsackie virus spikes into 1.25 mL of whole blood that was previously frozen once. Extractions were carried out using a modified version of the BCA protocol to test various conditions.

For each extraction 20 uL of Abbott Proteinase K was added to a 2 mL bead tube containing 900 mg of 0.2 mm Zirconnia/Yttria beads. 1.25 mL of blood was then added to each tube followed by 10 µL of the Coxsackie virus spike. Finally, 142 µL of 20% SDS was added to each bead tube. Each tube was then bead-beaten on the Precellys bead-beater at 6200 rpm for 3 sets of 90 sec. Following bead-beading the tubes were spun at 15 k rpm for 1 min to settle out the foam and bubbles.

One mL of lysate from each specimen was then transferred to a 2 mL screwcap tube. Each sample then got a different lysis treatment as detailed below:

To each tube was added 700 uL of a first wash buffer without any alcohol added. For samples 1 and 3 300 µL of the appropriate alcohol was added to the specimens. Each specimen was then mixed. Table 1 shows the alcohol used and when it was added for each sample

TABLE 1

| Sample | Alcohol used | Addition point for alcohol |
| --- | --- | --- |
| GCL120810CC-1 | Ethanol | Before lysis incubation |
| GCL120810CC-2 | Ethanol | After lysis incubation |
| GCL120810CC-3 | Isopropanol | Before lysis incubation |
| GCL120810CC-4 | Isopropanol | After lysis incubation |

Samples were incubated at 30° C. for 1 hour. Following the 1 h incubation, the appropriate alcohol was added to samples 2 and 4 and mixed. The samples then incubated for 5 min at room temperature.

All 2 mL of each sample was then added to a 24 DW kingfisher plate along with 160 µL of suspended magnetic particles. The elution plate was made using 250 µL of PDB. Second wash buffer plates were made up with ethanol according to the manufacturer instructions. The remaining kingfisher plates were also setup and loaded and the extraction protocol detailed below ran. For this protocol a single wash 1 and three wash 2 plates were used. After the extraction protocol the eluted samples were transferred to 1.5 mL screwcap tubes and placed on ice. A viral detection plate was loaded with RT enzyme mix and 5 µL of samples for rows F & G (the Coxsackie primers).

Samples were analyzed for the presence of Coxsackie virus with primer pairs complementary to the virus. 5 µL of eluted sample was added per well. The genomes per well was then recorded as shown in Table 2.

TABLE 2

| Sample | Genomes/well | |
|---|---|---|
| | PP VIR3758 | PP VIR3760 |
| GCL120810CC-1 | 119 | 309 |
| GCL120810CC-2 | 138 | 220 |
| GCL120810CC-3 | 571 | 194 |
| GCL120810CC-4 | 124 | 368 |

In each case RNA virus was detected. Better results were obtained when Isopropanol was used before the lysis incubation of 30-C for 1 hour.

In order to see how the RNA yield compared to an existing in-house method involving different isolation process, another set of extractions was performed. The protocol was the same as above with the exception that two first wash buffers with isopropanol were used instead of one and two second wash buffers used instead of three.

These samples were extracted alongside the other in house protocol using Qiagen DNEasy columns and bead beating. Coxsackie virus was then detected using primers (3578 and 3760) complementary to the virus. Results are shown in Table 3.

TABLE 3

| Sample | Extraction | Counts per well | | 3758 mean | 3760 mean |
|---|---|---|---|---|---|
| | | 3758 | 3760 | | |
| GCL120910CC-1 | TNA-BCA | 154 | 109 | 153.25 | 105.25 |
| GCL120910CC-2 | TNA-BCA | 160 | 101 | | |
| GCL120910CC-3 | TNA-BCA | 156 | 108 | | |
| GCL120910CC-4 | TNA-BCA | 143 | 103 | | |
| GCL120910CC-5 | Qiagen | 146 | 117 | 150.75 | 127 |
| GCL120910CC-6 | Qiagen | 160 | 125 | | |
| GCL120910CC-7 | Qiagen | 144 | 128 | | |
| GCL120910CC-8 | Qiagen | 153 | 138 | | |

The results show detection of RNA virus in the samples extracted with the new TNA-BCA method and that they were comparable to another method for the isolation of DNA and RNA from blood using silica-column based approach.

The extraction protocol was further optimized by looking at different conditions for the number of wash plates and the alcohol type used in second wash buffer plate. The same isolation protocol described above was used with blood spiked with Coxsackie virus. The variation between samples is shown in Table 4.

TABLE 4

| Condition | Notes | Number of replicates |
|---|---|---|
| TS-00050.01 | Per in-house protocol | 4 |
| TNA-BCA | Per protocol described above | 4 |
| TNA-BCA var1 | Varient of TNA-BCA; one Wash 1 with Isopropanol and three wash 2 with ethanol | 2 |
| TNA-BCA var2 | Varient of TNA-BCA; one Wash 1 with Isopropanol and three wash 2 with Isopropanol | 2 |

Following extraction the samples were run for detection of Coxsackie RNA virus. Results are shown in FIG. 1. Overall, a 3-4 fold increase in the RNA recovery as determined by virus detection was observed with the new protocol compared to existing methods. While some variations were noted between the different protocols they performed fairly similar.

To demonstrate that less DNA was not recovered as a result of also capturing RNA, both canine blood infected with *Dirofiliaria immitis* (heartworm, DNA detection based) and donor human blood were analyzed. Each sample was analyzed using a single first wash buffer with isopropanol and three second wash buffers with ethanol.

Figure 2:
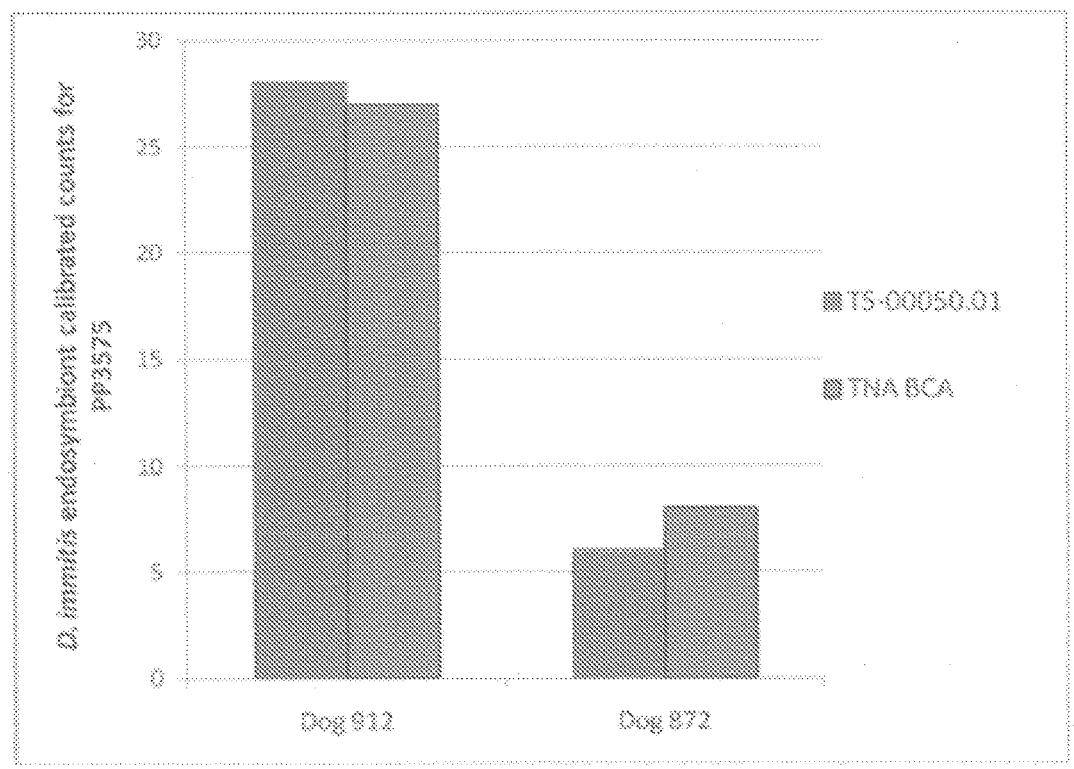
FIG. 2 shows detection of DNA isolated from the *Wolbachia endosymbiont* of *D. immitis* using methods of embodiments of the present invention.

Samples were then analyzed for the presence of the *Wolbachia endosymbiont* of *D. immitis* and the results between the two extraction methods compared (FIG. 2). The results showed that DNA recovery was not reduced in the new protocol compared to the original protocol.

Figure 3:
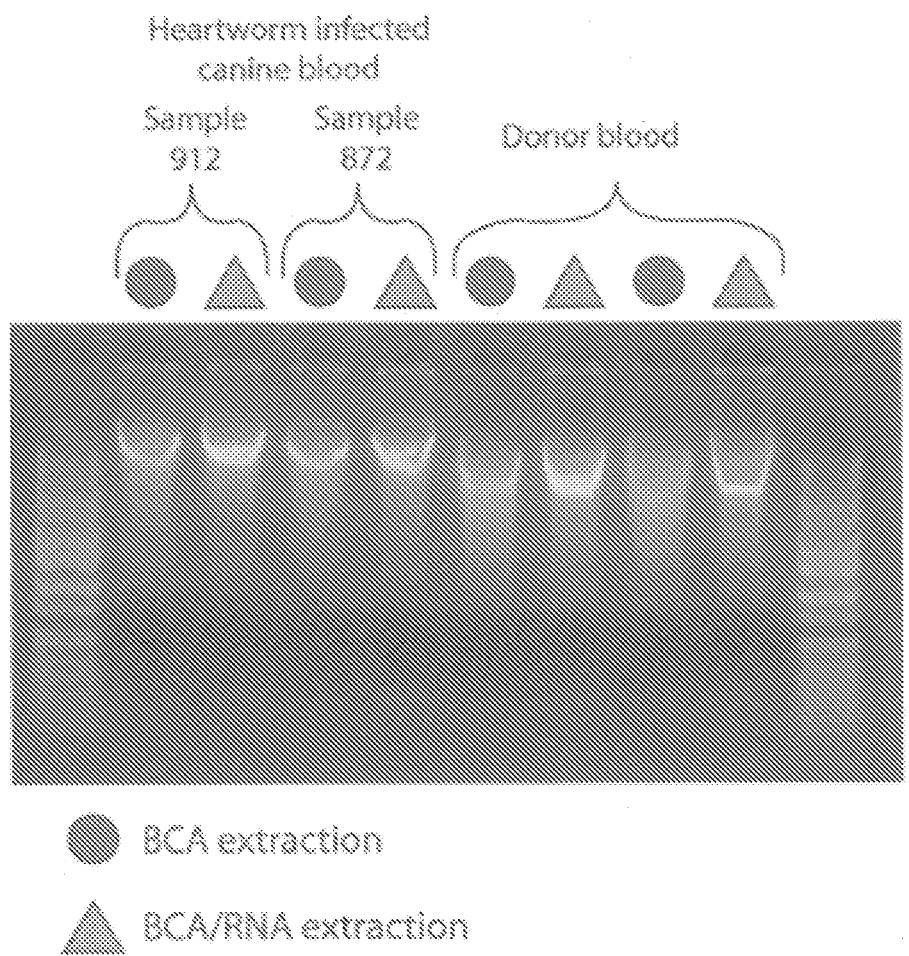
FIG. 3 shows a 1% agarose gel showing the recovery of nucleic acids from samples.

A 1% agarose gel was also run to visualize the recovery of nucleic acids from the samples. Nine µL of sample was loaded per well (FIG. 3).

The protocol's ability to recover nucleic acids from urine samples was also demonstrated. Urine was collected from a person experiencing illness. A commercially available kit using a different methodology was used as a comparator to the method for the ability to obtain nucleic acids from urine.

Figure 4:
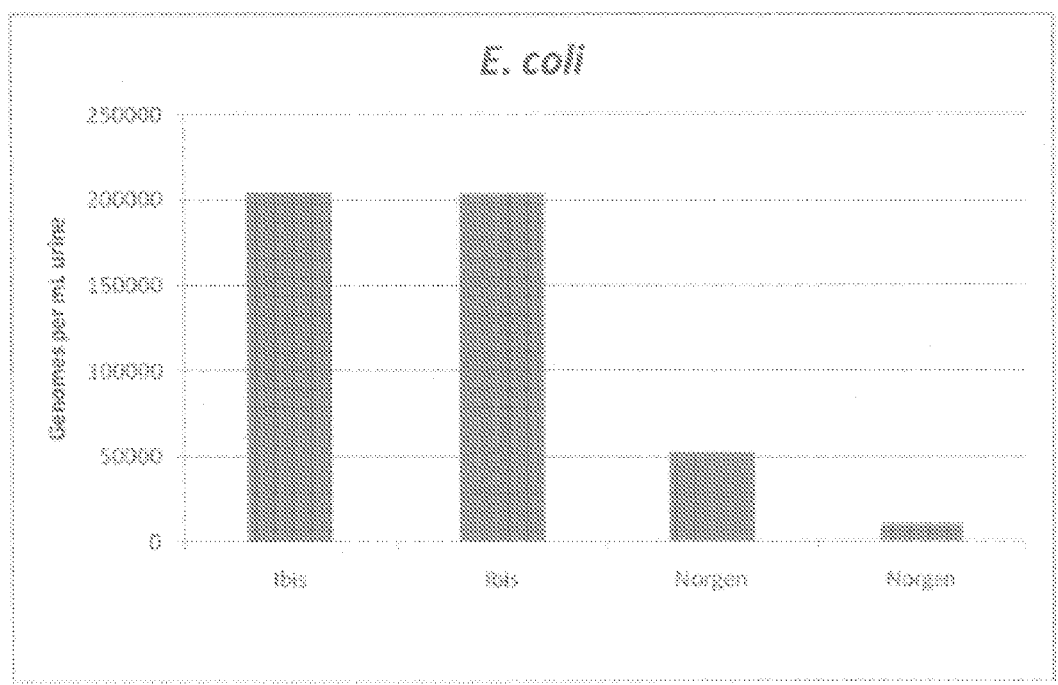
FIG. 4 shows recovery of *E. coli* from urine.

25 mL of urine was extracted from two different collections 1 day apart using a Norgen Urine DNA maxi kit following the manufacturer's instructions. 1.25 mL of urine was also extracted in duplicate following the TNA-BCA protocol described above. One addition to the protocol was that 6 µg of carrier RNA (Poly A; Ibis Biosciences) was added to each sample. Samples from each were analyzed for the presence of *E. coli* 0157. In all sample *E. coli* 0157 was detected showing the protocol obtained nucleic acids from the urine. The number of *E. coli* genomes per mL of urine from each method were calculated and compared (FIG. 4).

Figure 5:
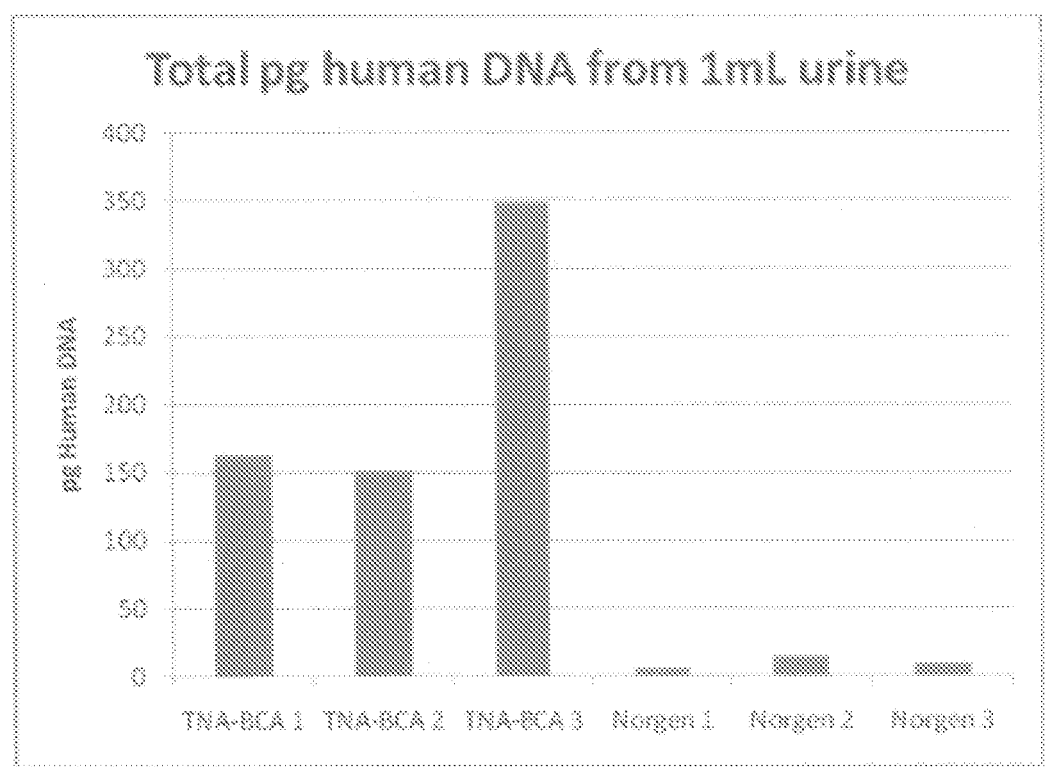
FIG. 5 shows recover of human DNA from urine using qPCR to the Alu gene.

To compare the ability of the protocol to extract nucleic acids from urine with a Norgen kit using the sample volume input, extractions were performed on 1 mL of donor urine in triplicate with both the TNA-BCA protocol and a Norgen Urine DNA Isolation Mini kit which can handle 50 µL to 2 mL of urine. Samples were then quantitated for the amount of human DNA recovered from the urine using qPCR to the Alu gene (FIG. 5).

The isolation of nucleic acids from urine was also demonstrated using the described protocol to detect the presence of pathogens in the urine of patients with accompanying blood samples drawn the same day. Extracted specimens were analyzed for the presence of tick-borne pathogens. In each of the urine specimens it was possible to detect the same pathogenic organism found in the patient's blood showing the protocol's use for isolating pathogen nucleic acids from urine.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

We claim:

1. A method of simultaneously extracting DNA and RNA from a sample, comprising:
   a) disrupting cells in said sample; then
   b) contacting said sample comprising said disrupted cells with a lysis solution comprising isopropanol to generate a mixture of said sample comprising said disrupted cells, said lysis solution and said isopropanol; then
   c) mixing said mixture; then
   d) incubating said mixture to generate a lysed sample; and then
   e) extracting nucleic acids from said lysed sample to generate extracted nucleic acids.

2. The method of claim 1, wherein said sample is an aqueous biological fluid.

3. The method of claim 2, wherein said aqueous biological fluid is selected from the group consisting of blood, blood products, and urine.

4. The method of claim 1, wherein said incubating comprises incubating at 30° C. for 1 hour.

5. The method of claim 1, further comprising the step of analyzing said extracted nucleic acids from said sample for the presence of a target DNA and/or RNA.

6. The method of claim 5, wherein said target nucleic acid is a pathogen nucleic acid.

7. The method of claim 6, wherein said pathogen is selected from the group consisting of a virus, a fungi, and a bacterium.

8. The method of claim 5, wherein said analyzing comprises a method selected from the group consisting of an amplification method, a sequencing method, and a hybridization method.

9. The method of claim 1, wherein said disrupting comprises bead beating in the presence of a detergent.

10. The method of claim 1, wherein said extracting step e) comprises binding said nucleic acids to a bead or solid support.

11. The method of claim 1, wherein said method is automated.

12. The method of claim 1, wherein said disrupting comprises a proteinase.

13. The method of claim 1, wherein said isopropanol is 15% isopropanol.

14. A method of simultaneously extracting DNA and RNA from a sample, comprising:
   a) bead beating said sample in the presence of a detergent and/or a proteinase to generate disrupted cells in said sample; then
   b) contacting said sample comprising said disrupted cells with isopropanol; then
   c) contacting said sample comprising said disrupted cells with said isopropanol with a lysis solution; then
   d) mixing said sample comprising said disrupted cells with said isopropanol with said lysis solution; then
   e) incubating said sample comprising said disrupted cells with said isopropanol with said lysis solution at 30° C. for one hour to generate a lysed sample; then
   f) extracting DNA and RNA from said lysed sample to generate extracted DNA and RNA.

* * * * *